United States Patent [19]
Minami

[11] Patent Number: 5,797,837
[45] Date of Patent: Aug. 25, 1998

[54] ENDOSCOPE IMAGE UNIT WITH CIRCUIT BOARD HAVING A HOLE THERETHROUGH

[75] Inventor: Itsuji Minami, Omiya, Japan

[73] Assignee: Fuji Photo Optical Co., Ltd., Omiya, Japan

[21] Appl. No.: 705,158

[22] Filed: Aug. 29, 1996

[30] Foreign Application Priority Data

Oct. 4, 1995 [JP] Japan .................................. 7-282553

[51] Int. Cl.$^6$ ................................................. A61B 1/05
[52] U.S. Cl. .............................. 600/109; 600/130; 348/76
[58] Field of Search .............................. 600/109, 110, 600/112, 129, 130; 348/65, 71, 75, 76, 294, 340, 338

[56] References Cited

U.S. PATENT DOCUMENTS 4,964,697 10/1990 Fuziwara .................................. 350/319
5,040,069 8/1991 Matsumoto et al. ...................... 348/76
5,430,475 7/1995 Goto et al. .................................. 348/65

*Primary Examiner*—John P. Leubecker
*Attorney, Agent, or Firm*—Ronald R. Snider

[57] ABSTRACT

An assembled body of an electronic endoscope which is capable of reducing the diameter of the endoscope and simplifying the structure thereof. The assembled body comprises an imaging device provided with a color filter and a microlens on the imaging plane, and an objective optical member connected to the imaging device. A circuit board with a wiring pattern and a through hole formed thereon and therein is inserted and adhered between the imaging plane of the imaging device and a prism as a part of the objective optical member. The terminals on the imaging device are connected to the terminals on the circuit board by contact bonding. Since the through hole in the circuit board forms an air gap on the imaging plane, it is possible to protect the color filter and the microlens.

1 Claim, 5 Drawing Sheets

ENDOSCOPE IMAGE UNIT WITH CIRCUIT BOARD HAVING A HOLE THERETHROUGH

BACKGROUND OF THE INVENTION

This application claims the priority of Japanese Patent Application No. 7-282553 filed on Oct. 4, 1995 which is incorporated herein by reference.

1. Field of the Invention

The present invention relates to a structure of an assembled body which is provided in an imaging portion of an electronic endoscope and which incorporates an imaging device having a color filter and a microlens.

2. Description of the Related Art

FIG. 6 is a side elevational view of an assembled body which is provided at the end portion of an electronic endoscope and which incorporates an imaging device. In the structure shown in FIG. 6, a cover glass 4 is connected to a lens barrel portion 2 having an objective lens system 1 via a prism 3, and the cover glass 4 is disposed at the position which enables the cover glass 4 to close the opening in the upper surface of a package 5. A CCD (charged coupled device) 6 as a solid-state image sensor is disposed within the package 5, and the package 5 is mounted on a circuit board 7. Therefore, the CCD 6 is also electrically connected to the circuit board 7 via the package 5.

The CCD 6 is, for example, an interline CCD, and a color filter (not shown) and a microlens (not shown) are provided on the imaging plane on the upper surface of the CCD 6. The color filter is provided so as to obtain a color image using, for example, a complementary color mosaic, while the microlens is provided so as to increase the light incidence efficiency with respect to the photosensor of the CCD 6. The CCD 6 provided with the color filter is attached to the interior of the package 5 in an airtight state (the package 5 is sometimes filled with degeneration preventive gas) so as to prevent the color of the color filter from changing.

FIG. 7 shows the interior of the end portion of the endoscope seen from the front side. The assembled body obtained by sequentially assembling the lens barrel portion 2 to the circuit board 7 is disposed on the upper side of the end portion 8. Light guides 9A, 9B are disposed on both sides of the objective lens system 1 in the vicinity thereof, and a tool insertion channel 10 for guiding a tool such as forceps is provided on the underside of the circuit board 7. According to this structure, when light is projected into the body as the object of inspection through the light guides 9A, 9B, the image of the internal body is caught by the CCD 6 via the objective lens system 1.

The great problems confronting a conventional endoscope are how to reduce the diameter of the end portion and how to simplify the structure of the endoscope. Especially, a reduction in the diameter of the end portion of an endoscope for the bronchi is in strong demand. In order to meet this demand, attention is paid to the assembled body of an imaging device in the present invention. As shown in FIG. 7, the cover glass 4, the package 5 and the circuit board 7 occupy the length of t1 in the diametrical direction of the end portion 8, t1 being equivalent to the sum of the thicknesses of these elements 4, 5 and 7. In other words, if the thickness t1 is reduced, it is possible to reduce the diameter of the end portion 8.

SUMMARY OF THE INVENTION

Accordingly, it is an object of the present invention to eliminate the above-described problems in the related art and to provide an assembled body of an imaging device in an electronic endoscope which is capable of reducing the diameter of the endoscope and simplifying the inner structure of the endoscope.

To achieve this end, an assembled body of an imaging device in an electronic endoscope according to the present invention comprises: an objective optical member; an imaging device having an imaging plane for imaging an object of inspection caught by the objective optical member and provided with at least either of a color filter and a microlens provided on the imaging plane; a signal wire for transmitting a signal to the imaging device; and a circuit board provided with an air gap portion for forming an air gap and a wiring pattern for connecting the imaging device with the circuit board on the imaging plane; wherein the circuit board is inserted between and adhered to the imaging plane of the imaging device and the objective optical member.

It is preferable to provide a through hole in the circuit board as the air gap portion.

It is possible to connect terminals which are formed as a part of the wiring pattern on the circuit board and terminals formed on the imaging plane of the imaging device by contact bonding.

If the objective optical member includes a prism, the circuit board is adhered to the bottom surface of the prism. On the other hand, if the objective optical member does not include a prism, the circuit board is adhered to the rear end surface of the objective optical member.

According to this structure, for example, a color filter is provided on the surface of an imaging device, and a microlens is provided on the color filter. A circuit board having a, for example, circular opening (through hole) and a wiring pattern is directly adhered to the microlens with an adhesive. The size of the opening is determined in accordance with an imaging range, and the wiring pattern is printed on the circuit board so as to electrically connect projecting terminals provided on the imaging device with signal wires. Terminals formed as a part of the wiring pattern and the projecting terminals of the imaging device are contact bonded by using, for example, a bumper and an adhesive. An objective optical member is adhered to the opposite side of the circuit board with an adhesive so as to keep the opening in an airtight state.

In such an assembled body, the opening formed in the circuit board serves as the air gap which is provided in the upper portion of a conventional package. Therefore, if it is assumed that the circuit board and the cover glass of the package have the same thickness, the length of the assembled body of the present invention in the diametrical direction of the endoscope is reduced by the length corresponding to the air gap provided in the upper portion of the conventional package. In addition, since the conventional circuit board disposed on the underside of the imaging device is dispensed with, the length is also reduced by the length corresponding to the thickness of the conventional circuit board.

The above and other objects, features and advantages of the present invention will become clear from the following description of the preferred embodiments thereof, taken in conjunction with the accompanying drawings.

DESCRIPTION OF THE PREFERRED EMBODIMENTS

Figure 1:
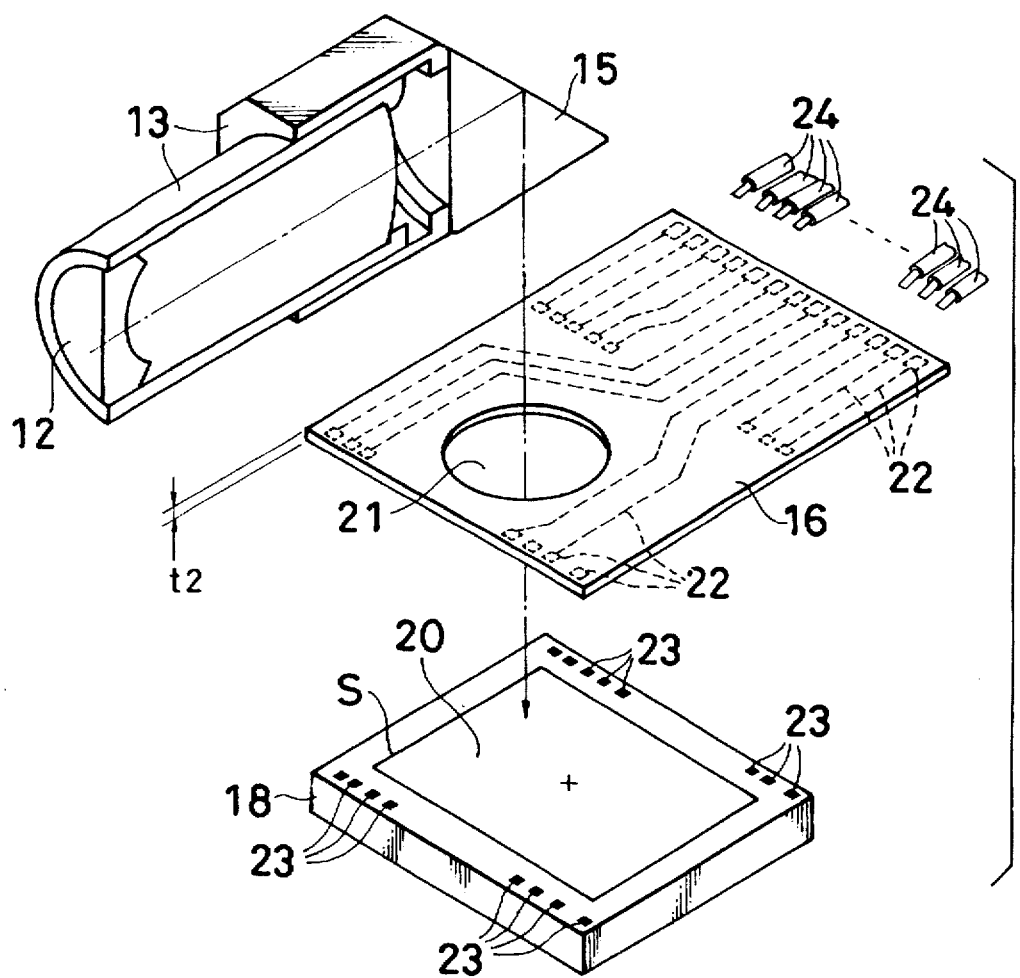
FIG. 1 is an exploded perspective view of a first embodiment of an assembled body of an imaging device in an electronic endoscope according to the present invention.
Figure 2:
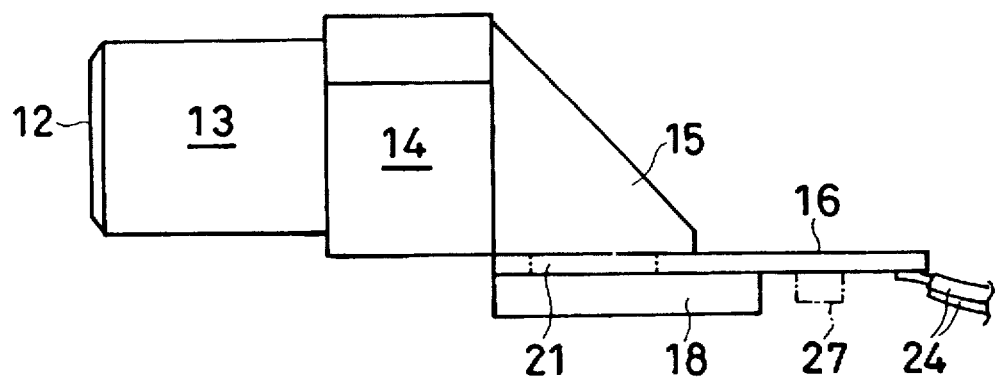
FIG. 2 shows the assembled body shown in FIG. 1 in the assembled state.
Figure 3:
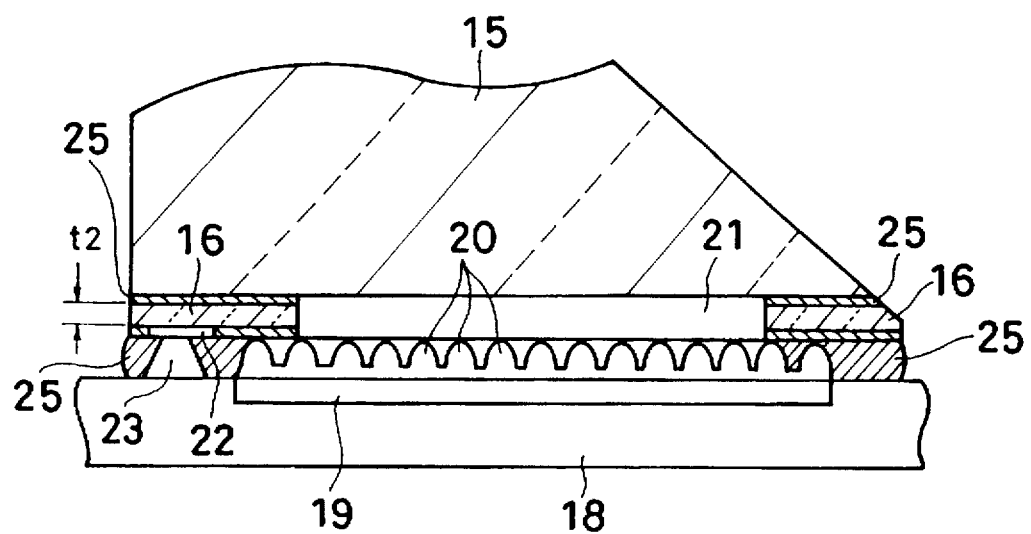
FIG. 3 is an explanatory view of the structure of the connecting portion between the CCD and the circuit board in the first embodiment.

FIG. 1 is an exploded perspective view of a first embodiment of an assembled body of an imaging device in an electronic endoscope according to the present invention, FIG. 2 shows the assembled body in the assembled state, and FIG. 3 shows the connecting portion between the imaging device and the circuit board. The elements shown in FIG. 1 are disposed at the end portion of an endoscope. A prism 15 is connected to a lens barrel portion 13 having an objective lens system 12, an optical filter, etc. A CCD 18 is disposed on the underside bottom of the prism 15 via a circuit board 16. The CCD 18 is provided with a color filter 19 on the imaging plane on the upper surface thereof, as shown in FIG. 3, and a microlens 20 (schematically enlarged in FIG. 3) is provided on the color filter 19.

The circuit board 16 is made of a synthetic resin, ceramic, metal or the like, and it has a predetermined thickness t2 (about 0.1 to several mm). The circuit board 16 may be a flexible board. A circular opening 21 is formed in the circuit board 16. The size of the opening 21 is determined to be a predetermined size so that the opening 21 is contained in the imaging range S of the CCD 18, as shown in FIG. 1. A wiring pattern 22 is formed on the back side of the circuit board 16, and projecting terminals (electrodes) 23 are provided on the upper surface of the CCD 18, as shown in FIG. 1. On the circuit board 16, therefore, the projecting terminals 23 are connected to the terminals of the wiring pattern 22 and the terminals on the rear end side are connected to signal wires 24.

The elements shown in FIG. 1 are assembled in this manner, so that the assembled body shown in FIG. 2 is obtained. The opening 21 is disposed at a predetermined position and the positions of the projecting terminals 23 on the CCD 18 and the terminals of the wiring pattern 22 are matched. In this state, the circuit board 16 is directly adhered to the upper surface of the CCD 18 with an adhesive 25 by using a bumper or the like. The projecting terminals are almost crushed and, in this state, connected to the terminals of the wiring pattern 22. A prism is adhered to the upper surface of the circuit board 16 with the adhesive 25. A circuit member 27 such as a CCD driving circuit may be disposed on the underside of the circuit board 16, as shown in FIG. 2.

According to this structure, the opening 21 in the circuit board 16 is maintained in an airtight state, and it is possible to fill the opening 21 with a predetermined color filter degeneration preventive gas. Since the CCD 18 is electrically connected to the signal wires 24 via the circuit board 16, it is possible to take out video signals obtained by the CCD 18 to the outside via the signal wires 24.

Figure 6:
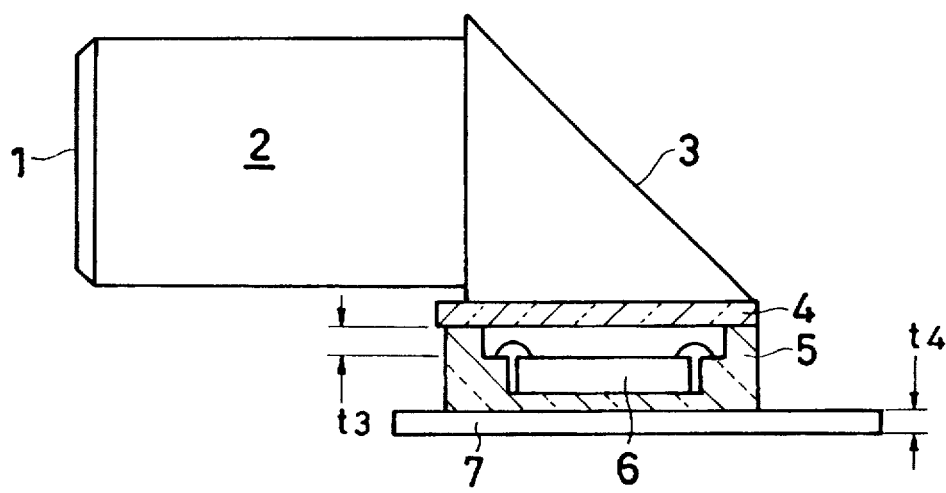
FIG. 6 shows the structure of a conventional assembled body of an imaging device.
Figure 7:
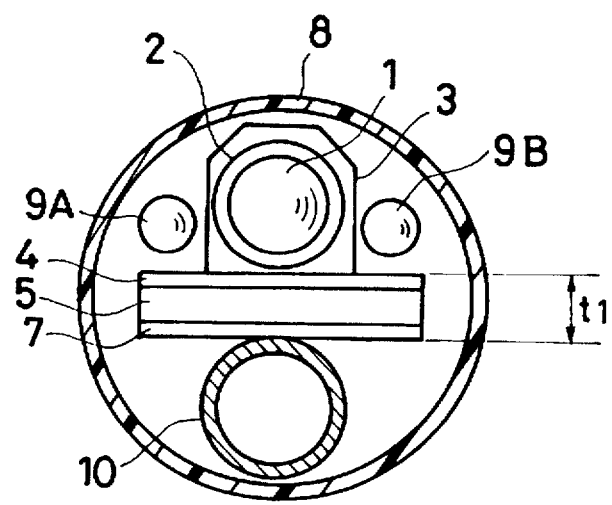
FIG. 7 is a front view of the interior of an endoscope using the conventional assembled body shown in FIG. 6.

According to the first embodiment, the opening 21 forms an air gap having a height of t2 between the CCD 18 (microlens 20) and the prism 15, which obviates the air gap t3 in the package 5 shown in FIG. 6. In addition, since the conventional circuit board 7 disposed on the underside of the CCD 18 is dispensed with, the length of the assembled body in the diametrical direction of the endoscope is reduced by the length which corresponds to the thickness t4 of the circuit board 7 shown in FIG. 6. It is therefore possible in this embodiment to reduce the length of the assembled body in the diametrical direction (in the vertical direction in the drawings) of the endoscope by the length which corresponds to the air gap t3 and the thickness t4 of the circuit board 7, thereby contributing to the reduction in the diameter of the endoscope.

Owing to the existence of the airtight space in the opening 21 in the circuit board 16, it it possible to prevent the color of the color filter 19 from changing due to degeneration or the like. When this embodiment is compared with the structure shown in FIG. 6, since light from the lens barrel portion 2 does not pass the cover glass 4, it is possible to enhance the light collecting efficiency of the microlens 20.

Figure 4:
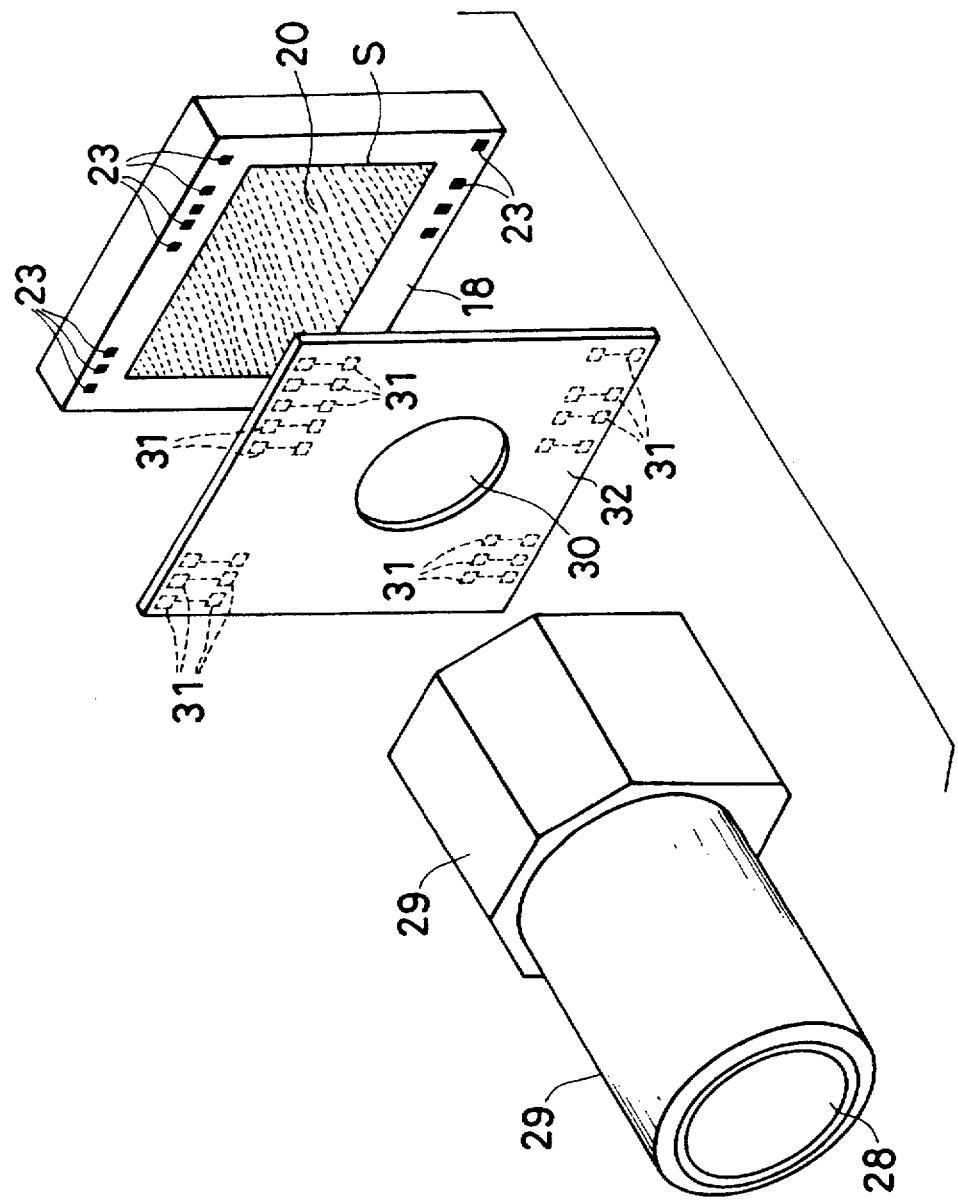
FIG. 4 is an exploded perspective view of a second embodiment of an assembled body of an imaging device in an electronic endoscope according to the present invention.

FIG. 4 shows the structure of a second embodiment of the present invention. This embodiment is not provided with a prism. As shown in FIG. 4, a lens barrel portion 29 having an objective lens system 28, an optical filter, etc. are also provided. The objective optical member 28, 29 has circuit board 32 adhered to the rear end surface of lens barred portion 29. The CCD 18 as an imaging device is disposed vertically with respect to the optical axis of the lens barrel portion 29. A circuit board 32 with an opening 30 formed therein is inserted between the CCD 18 and the attached to the CCD 18 after the projecting terminals 23 are connected to predetermined terminals on the circuit board 32. The circuit board 32 is connected in the same way as in the first embodiment so as to keep the opening 30 in an airtight state.

According to the second embodiment of an assembled body, the length of the assembled body in the diametrical direction of the endoscope is reduced by the length which corresponds to the sum of the air gap t3 in the package 5 and the thickness t4 of the circuit board 7 shown in FIG. 6. Therefore, if the second embodiment is used for a side-looking type endoscope, it is possible to reduce the diameter of the endoscope.

In the first and second embodiments, the opening 21 (30) in the circuit boards 16 (32) is circular, but the size and the shape of t he opening can be freely set within the imaging range S of the CCD 18.

Figure 5:
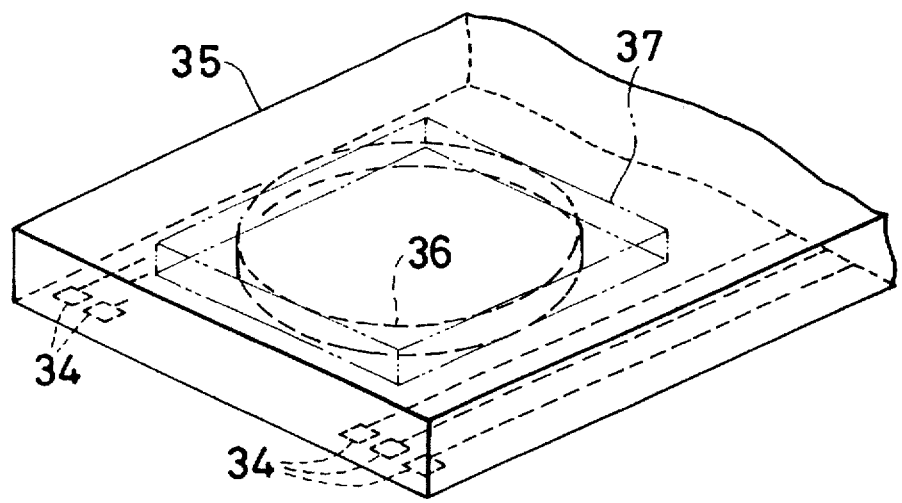
FIG. 5 shows the internal structure of the end portion of the circuit board in a third embodiment of the present invention.

FIG. 5 shows the structure of a third embodiment of the present invention. In this embodiment, a groove for forming a n air gap is formed in a transparent circuit board. As shown in FIG. 5, a circular groove 36 having a depth smaller than the thickness of a circuit board 35 provided with a wiring pattern 34 is formed in the undersurface of the circuit board 35, and the circuit board 35 is used in place of the circuit board 16 in the first embodiment or the circuit board 32 in the second embodiment. Such a circular groove 35 in the circuit board 35 serves as an air gap above the imaging plane. It is also possible to form a rectangular groove 37 having the same depth in the circuit board 35, as indicated by the two-dot chain line in FIG. 5.

Although both the color filter 19 and the microlens 20 are provided on the CCD 18 in each embodiment, the present invention is also applicable to an imaging device which is provided only with either the color filter 19 or the microlens 20.

As explained above, according to the present invention, it is possible to arrange an air gap on the imaging plane with a good efficiency, a cover glass is obviated, and it is possible to reduce the length of the assembled body in the diametrical direction of the endoscope by the length which corresponds to the thickness of a conventional circuit board. It is therefore possible to reduce the diameter of the endoscope.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. Electronic endoscope unit comprising:

an objective optical member;

an imaging device having an imaging plane and an upper surface for imaging an object of inspection which is caught by said objective optical member and provided with at least either of a color filter and a micro-lens provided on said imaging plane;

a signal wire for transmitting a signal from said imaging device;

a circuit board provided with an air gap portion for forming an entire air gap between the objective optical member and the color filter or micro-lens, and a wiring pattern for connecting said imaging device with said circuit board on said surface;

wherein said circuit board is inserted between and adhered to said upper surface of said imaging device and said objective optical member;

wherein said air gap on said circuit board is a through hole;

wherein the circuit board is adhered between the upper surface of said imaging device and said objective optical member with an adhesive so that said through hole is maintained in an air-tight state;

wherein said wiring pattern and said imaging device are provided with respective terminals, whereby said respective terminals are connected by contact bonding; and wherein said objective optical member includes a prism and said circuit board is adhered to a bottom surface of said prism.

* * * * *